United States Patent
Burrows et al.

(10) Patent No.: US 9,464,057 B2
(45) Date of Patent: Oct. 11, 2016

(54) ANTI-MALARIAL AGENTS

(71) Applicants: MMV MEDICINES FOR MALARIA VENTURE, Geneva (CH); DREXEL UNIVERSITY, Philadelphia, PA (US); UNIVERSITY OF WASHINGTON, Seattle, WA (US)

(72) Inventors: Jeremy Burrows, La Rippe (CH); Matthew Wyvratt, Mountainside, NJ (US); Akhil Vaidya, Wynnewood, PA (US); Sandhya Kortagere, Newtown, PA (US); Erkang Fan, Shoreline, WA (US); Arnab Kumar Chatterjee, San Diego, CA (US); Advait Suresh Nagle, San Diego, CA (US); Tomoyo Kato, Cambridge, MA (US)

(73) Assignees: MMV MEDICINES FOR MALARIA VENTURE, Geneva (CH); DREXEL UNIVERSITY, Philadelphia, PA (US); UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 14/905,369

(22) PCT Filed: Jul. 17, 2014

(86) PCT No.: PCT/IB2014/063180
§ 371 (c)(1),
(2) Date: Jan. 15, 2016

(87) PCT Pub. No.: WO2015/008246
PCT Pub. Date: Jan. 22, 2015

(65) Prior Publication Data
US 2016/0194286 A1   Jul. 7, 2016

Related U.S. Application Data

(60) Provisional application No. 61/847,185, filed on Jul. 17, 2013.

(51) Int. Cl.
*C07D 403/12* (2006.01)
*C07D 231/40* (2006.01)
*A61K 31/4184* (2006.01)
*A61K 45/06* (2006.01)
*A61K 31/415* (2006.01)

(52) U.S. Cl.
CPC ............ *C07D 231/40* (2013.01); *A61K 31/415* (2013.01); *A61K 31/4184* (2013.01); *A61K 45/06* (2013.01); *C07D 403/12* (2013.01)

(58) Field of Classification Search
None
See application file for complete search history.

(56) References Cited

FOREIGN PATENT DOCUMENTS

WO   WO 2009/065096   5/2009

OTHER PUBLICATIONS

Written Opinion in International Application No. PCT/IB2014/063180, Oct. 22, 2014, pp. 1-5.
Desjardins, R.E., et al., "Quantitative Assessment of Antimalarial Activity In Vitro by a Semiautomated Microdilution Technique," *Antimicrobial Agents and Chemotherapy*, Dec. 1979, vol. 16, No. 6, pp. 710-718.
Jiménez-Díaz, M.B., et al., "Improved Murine Model of Malaria Using *Plasmodium falciparum* Competent Strains and Non-Myelodepleted NOD—*scid IL2R$\gamma^{null}$* Mice Engrafted with Human Erythrocytes," *Antimicrobial Agents and Chemotherapy*, Oct. 2009, vol. 53, No. 10, pp. 4533-4536.
Kortagere, S., et al., "Structure-based Design of Novel Small-Molecule Inhibitors of *Plasmodium falciparum*," *Journal of Chemical Information and Modeling*, 2010, vol. 50, No. 5, pp. 840-849.
Marfurt, J., et al., "Ex Vivo Activity of Histone Deacetylase Inhibitors against Multidrug-Resistant Clinical Isolates of *Plasmodium falciparum* and *P. vivax*," *Antimicrobial Agents and Chemotherapy*, Mar. 2011, vol. 55, No. 3, pp. 961-966.
Vaidya, A.B., et al., "Pyrazoleamide compounds are potent antimalarials that target NA$^+$homeostasis in intraerythrocytic *Plasmodium falciparum*," *Nature Communications*, Nov. 25, 2014, DOI: 10.1038/ncomms6521, pp. 1-10.

*Primary Examiner* — Laura L. Stockton
(74) *Attorney, Agent, or Firm* — Saliwanchik, Lloyd & Eisenschenk

(57) ABSTRACT

The present invention is related to a use of pyrazole derivatives in the manufacture of a medicament for preventing or treating malaria. Specifically, the present invention is related to pyrazole derivatives useful for the preparation of a pharmaceutical formulation for the inhibition of malaria parasite proliferation.

10 Claims, No Drawings

US 9,464,057 B2

ANTI-MALARIAL AGENTS

CROSS-REFERENCE TO RELATED APPLICATIONS

This application is the U.S. national stage application of International Patent Application No. PCT/IB2014/063180, filed Jul. 17, 2014, which claims the benefit of U.S. Provisional Patent Application No. 61/847,185, filed Jul. 17, 2013.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum* is the dominant species in sub-Saharan Africa, and is responsible for the almost 1 million deaths each year. The disease burden is heaviest in African children under 5 years of age and in pregnant women. *Plasmodium vivax* causes 25-40% of the global malaria burden, particularly in South and Southeast Asia, and Central and South America. The other three main species that are known to infect humans are *Plasmodium ovale, Plasmodium knowelsi* and *Plasmodium malariae*. Malaria is a disease that is prevalent in many developing countries. Approximately 40% of the world's population lives in countries where the disease is endemic; approximately 247 million people suffer from the disease every year.

Various medications are presently used for the treatment of malaria. However, many of these medications are costly and some exhibit significant toxicity and undesirable side effects in humans. Drugs used for treating malaria include artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-,(1'R,3'S)—], Sulfur, [4-[[2-(1,1-difluoroethyl)-5-methyl[1,2,4]triazolo [1,5-a]pyrimidin-7-yl]amino]phenyl] pentafluoro-] (CAS Registry Number: 1282041-94-4), Morpholine, and 4-[2-(4-cis-dispiro[cyclohexane-1,3'-[1,2,4]trioxolane-5',2"-tricyclo [3.3.1.13,7]decan]-4-ylphenoxy)ethyl]-] (CAS Registry Number: 1029939-86-3). However, the widespread emergence of drug resistance of malaria parasites in many tropical countries has compromised many of the current chemotherapies and there is a continued need for new chemotherapeutic approaches.

Some pyrazole derivatives have been said to be able to induce some inhibition of growth of *P. falciparum* strain 3D7 and Dd2 parasites (WO 2009/065096). However, those molecules do not possess sufficient potency, physical properties and pharmacokinetics to show significant oral efficacy in murine disease models of malaria. Accordingly, this invention provides novel potent anti-malarial agents and methodology of treating malaria using novel potent anti-malarial agents.

SUMMARY OF THE INVENTION

The present invention is directed towards novel pyrazole derivatives that are useful in the treatment and/or prophylaxis of malaria, pharmaceutical formulation, use and manufacture thereof.

A first aspect of the invention provides a pyrazole derivative according to the invention or a pharmaceutically acceptable salt thereof.

A second aspect of the invention relates to pyrazole derivative or a pharmaceutically acceptable salt thereof according to the invention for use as a medicament.

A third aspect of the invention relates to the use of pyrazole derivative according to the invention or a pharmaceutically acceptable salt thereof, for the preparation of a pharmaceutical composition for the prevention and/or treatment of malaria.

A fourth aspect of the invention resides in a pharmaceutical formulation comprising at least one pyrazole derivative according to the invention or a pharmaceutically acceptable salt thereof, and a pharmaceutically acceptable carrier, diluent or excipient thereof.

A fifth aspect of the invention relates to a pyrazole derivative according to the invention or a pharmaceutically acceptable salt thereof, for use in the prevention and/or treatment of malaria.

A sixth aspect of the invention resides in a method for preventing and/or treating malaria in a patient. The method comprises administering a pyrazole derivative according to the invention or a pharmaceutically acceptable salt in a patient in need thereof.

A seventh aspect of the invention provides a process for the preparation of a pyrazole derivative according to the invention or a pharmaceutically acceptable salt thereof according to the invention and intermediates thereof.

An eighth aspect of the invention provides a method for inactivating parasitic infection in a cell comprising the step of contacting the cell with an effective amount of at least one compound according to the invention.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "pharmaceutically acceptable salts or complexes" refers to salts or complexes of the compounds according to the invention. Examples of such salts include, but are not restricted, to base addition salts formed by reaction of pyrazole derivatives of the invention with organic or inorganic bases such as hydroxide, carbonate or bicarbonate of a metal cation such as those selected in the group consisting of alkali metals (sodium, potassium or lithium), alkaline earth metals (e.g. calcium or magnesium).

Are also comprised salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, benzene sulphonic acid, methane sulphonic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically. These compounds can be produced from compounds of the present invention according to well-known methods.

The term "indirectly" also encompasses metabolites of compounds according to the invention.

The term "metabolite" refers to all molecules derived from any of the compounds according to the present invention in a cell or organism, preferably mammal.

The term "malaria" includes disease and conditions related to an infection by *Plasmodium*.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount" and can refer to the amount used as part of a combination. The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used. According to one embodiment, the malaria parasites are *P. falciparum* and *P. vivax*.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

According to one embodiment, is provided a pyrazole derivative according to Formula (I):

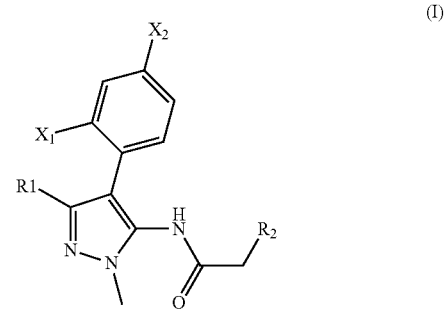

wherein $X_1$ is selected from F and H; $X_2$ is selected from Cl and F; $R^1$ is selected from methyl and trifluoromethyl; $R^2$ is selected from the following groups:

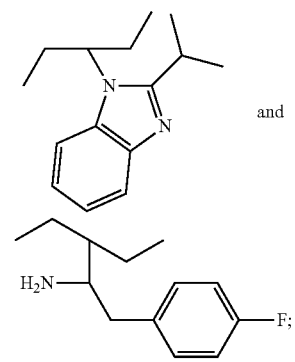

as well as any pharmaceutically acceptable salt, hydrate, solvate, polymorph, tautomers, geometrical isomers, or optically active isomers thereof.

In a particular embodiment, the invention provides a pyrazole derivative according to the invention wherein $R^2$ is:

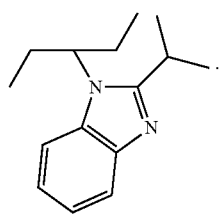 [SMILES: CCC(CC)n1c(C(C)C)nc2ccccc21]

In a particular embodiment, the invention provides a pyrazole derivative according to the invention wherein $R^2$ is

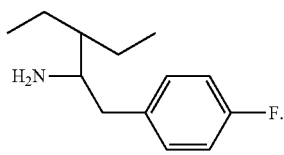

In a particular embodiment is provided a pyrazole derivative selected from the following group:
N-(4-(4-chloro-2-fluorophenyl)-3-(trifluoromethyl)-1-methyl-1H-pyrazol-5-yl)-2-(2-isopropyl-1H-benzo[d]imidazol-1-yl)acetamide;
N-(4-(4-chloro-2-fluorophenyl)-1,3-dimethyl-1H-pyrazol-5-yl)-2-(2-isopropyl-1H-benzo[d] imidazol-1-yl)acetamide;
3-amino-N-(3-(trifluoromethyl)-4-(4-fluorophenyl)-1-methyl-1H-pyrazol-5-yl)-4-(4-fluorophenyl)butanamide; and
3-amino-4-(4-fluorophenyl)-N-(4-(4-fluorophenyl)-1,3-dimethyl-1H-pyrazol-5-yl)butanamide; as well pharmaceutically acceptable salt, hydrate, solvate, polymorph, tautomers, geometrical isomers, or optically active isomers thereof.

In a further particular embodiment, is provided a pyrazole derivative selected from the following group:
N-(4-(4-chloro-2-fluorophenyl)-3-(trifluoromethyl)-1-methyl-1H-pyrazol-5-yl)-2-(2-isopropyl-1H-benzo[d]imidazol-1-yl)acetamide;
N-(4-(4-chloro-2-fluorophenyl)-1,3-dimethyl-1H-pyrazol-5-yl)-2-(2-isopropyl-1H-benzo[d] imidazol-1-yl)acetamide;
(R)-3-amino-N-(3-(trifluoromethyl)-4-(4-fluorophenyl)-1-methyl-1H-pyrazol-5-yl)-4-(4-fluorophenyl)butanamide; and
(R)-3-amino-4-(4-fluorophenyl)-N-(4-(4-fluorophenyl)-1,3-dimethyl-1H-pyrazol-5-yl)butanamide; as well pharmaceutically acceptable salt, hydrate, solvate, polymorph, tautomers.

The pyrazole derivatives used in the manufacture of a medicament for the prevention or treatment of malaria, are capable of killing and/or inhibiting malaria parasite replication and/or blocking transmission.

Compositions

The invention provides pharmaceutical compositions useful for the prophylaxis and/or treatment of malaria. The invention further provides methods for treating a mammalian patient, and most preferably a human patient, who is suffering from malaria.

In another particular embodiment, is provided a pharmaceutical formulation containing at least one derivative according the invention and a pharmaceutically acceptable carrier, diluent or excipient thereof.

In another particular embodiment, is provided a pharmaceutical formulation comprising a pyrazole according to Formula (I) and an antimalarial agent as defined in the detailed description.

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in *The Science and Practice of Pharmacy* (Remington: The Science & Practice of Pharmacy), $22^{nd}$ Edition, 2012, Lloyd, Ed. Allen, Pharmaceutical Press, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, rectally, or combinations thereof. Parenteral administration includes, but is not limited to, intravenous, intra-arterial, intra-peritoneal, subcutaneous, intramuscular, intrathecal, and intra-articular. The compositions of this invention may also be administered in the form of an implant, which allows slow release of the compositions as well as a slow controlled i.v. infusion. In a preferred embodiment, pyrazole derivatives according to the invention are administered orally. In a particular embodiment, compounds of the invention are administered at a dose to humans of between about 1 mg and 1'500 mg such as for example at about 50 mg. In a further particular embodiment, compound of the invention are administered at a dose of less than 500 mg.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

The compositions of this invention may be used in a method for inactivating parasitic infection in a cell comprising the step of contacting the cell with an effective amount of at least one compound according to the invention. According to a particular aspect, the cell is a primate cell such as a red blood cell for example a human cell.

Combination

According to the invention, the pyrazole derivatives of the invention and pharmaceutical formulations thereof can be administered alone or in combination with a co-agent useful in the treatment of malaria, such as substances useful in the treatment and/or prevention of malaria e.g. for example a co-agent including, but not limited to, artemisinin or an artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-,(1'R, 3'S)—], Sulfur, [4-[[2-(1,1-difluoroethyl)-5-methyl[1,2,4]triazolo [1,5-a]pyrimidin-7-yl]amino]phenyl] pentafluoro-] (CAS Registry Number: 1282041-94-4), Morpholine, and 4-[2-(4-cis-dispiro[cyclohexane-1,3'-[1,2,4]trioxolane-5', 2"-tricyclo [3.3.1.13,7]decan]-4-ylphenoxy)ethyl]-] (CAS Registry Number: 1029939-86-3).

The invention encompasses the administration of a pyrazole derivative according to the invention or of a pharmaceutical formulation thereof, wherein the pyrazole derivatives or the pharmaceutical formulation thereof is administered to an individual prior to, simultaneously or sequentially with other therapeutic regimens or co-agents useful in the treatment of malaria (e.g. multiple drug regimens), in an effective amount. Pyrazole derivatives or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium*.

In another embodiment, patients according to the invention are patients with a high risk of being infected by *Plasmodium falciparum*.

In another embodiment, patients according to the invention are patients with a high risk of being infected by *Plasmodium vivax*.

Use According to the Invention

In one embodiment, the invention provides a use of a pyrazole derivative according to Formula (I) as described herein, as well pharmaceutically acceptable salt, hydrate, solvate, polymorph, tautomers, geometrical isomers, or optically active forms thereof for the preparation of a pharmaceutical composition for the treatment or prophylaxis of malaria.

In another embodiment, the invention provides a method for preventing or treating malaria in a patient. The method comprises administering an effective amount of a pyrazole derivative according to the invention, or a pharmaceutically acceptable salt or a pharmaceutically active derivative thereof or a pharmaceutical formulation thereof in a patient in need thereof.

In another embodiment, the invention provides a pyrazole derivative according to the invention as well as pharmaceutically acceptable salts or a pharmaceutically active derivative thereof or a pharmaceutical formulation thereof, for use in the treatment or prophylaxis of malaria.

In another embodiment, the invention provides a use of a pyrazole derivative or a method according to the invention wherein the pyrazole derivative is to be administered in combination with a co-agent useful in the treatment of malaria.

In another embodiment, the invention provides a pharmaceutical composition comprising a pyrazole derivative according to the invention in combination with a co-agent useful in the treatment of malaria.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. In the following the present invention shall be illustrated by means of some examples, which are not to be viewed as limiting the scope of the invention.

EXAMPLES

The following abbreviations refer respectively to the definitions below:

DCM (dichloromethane), DBU (1,8-Diazabicyclo[5.4.0]undec-7-ene), HEPES (4-(2-hydroxyethyl)-1-piperazineethanesulfonic acid), LHM (Low hypoxanthine medium), MS (Mass Spectrometry), MHz (Megaherz), NMR (Nuclear magnetic resonance), MW (microwave), TEA (Triethyl amine), TFA (Trifluoroacetic acid), RBC (Red blood cell), THF (Tetrahydrofuran).

The compounds of invention have been named according to the IUPAC standards used in the program ChemDraw® 7.0. The MS and NMR data provided in the examples described below are obtained as followed: MS data was obtained from an Agilent 1100 LC/MSD Trap; proton NMR was recorder on a Bruker AV-500 at 500 MHz. All reagents and intermediates whose synthesis is not described were purchased from standard commercially available sources.

Example 1

Synthesis of Compounds According to the Invention

The pyrazole derivatives can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

N-(4-(4-chloro-2-fluorophenyl)-3-(trifluoromethyl)-1-methyl-1H-pyrazol-5-yl)-2-(2-isopropyl-1H-benzo[d]imidazol-1-yl)acetamide (Compound (1))

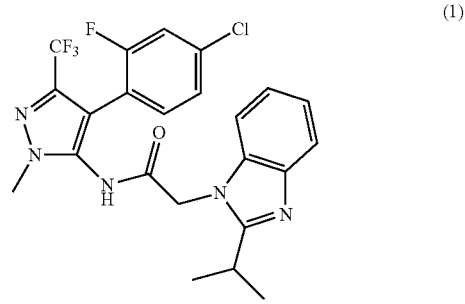 [SMILES: CC(C)c1nc2ccccc2n1CC(=O)Nc1c(-c2ccc(Cl)cc2F)c(C(F)(F)F)nn1C]

The title compound of the invention was synthesized as described in Scheme 1 below.

Scheme 1

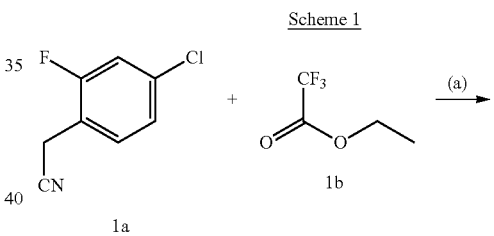

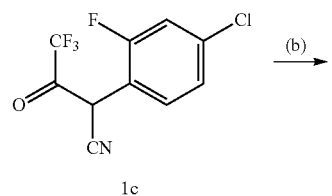

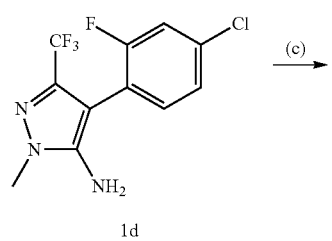

-continued

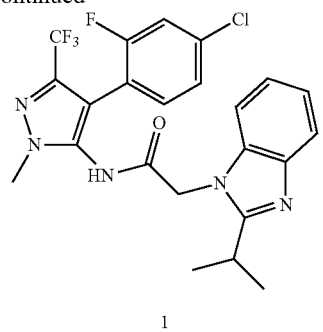

1

Reagents and conditions: (a) EtONa, EtOH, refluxing; (b) CH₃NHNH₂, HCl, EtOH, MW, 100° C., 40 min; (c) 2-(2-isopropyl-1H-benzo[d]imidazol-1-yl)acetic acid, Mukaiyama's reagent, TEA, DCM, THF, MW, 75° C., 30 min. A mixture of 1.8 ml (15 mmol) of ethyl 2,2,2-trifluoroacetate (1b) and 1.2 g (7.1 mmol) of 2-(4-chloro-2-fluorophenyl)acetonitrile (1a) in 10 ml of ethanol was slowly dropped into hot solution of 1.2 g of sodium in 20 ml of ethanol. The mixture was refluxed overnight. The solution turns red. After cooled down, the solution was poured into 250 ml of cold water acidified with 10 ml concentrated HCl. The mixture was extracted with ethyl acetate. The ethyl acetate extraction was washed with water, brine and dried over MgSO₄. Ethyl acetate was removed and the residual reddish oil of 2-(4-chloro-2-fluorophenyl)-4,4,4-trifluoro-3-oxobutanenitrile (1c) was obtained in 1.2 g. The raw material was dissolved in 10 ml of ethanol and used in next step without further purification. A mixture of 2 ml of the above ethanol solution and 72 µl of methylhydrazine with 0.14 ml of concentrated HCl was irradiated in microwave oven at 100° C. for 40 min. The solution was treated with saturated NaHCO₃ and extracted by ethyl acetate. The organic layer was washed with water, brine, dried over MgSO4 and concentrated. The yellow residue was subjected to flash chromatography purification with MeOH/DCM to give 120 mg of 4-(4-chloro-2-fluorophenyl)-3-(trifluoromethyl)-1-methyl-1H-pyrazol-5-amine (1d) as light yellow solid. M/Z=294.6 (M+1). To a mixture of 2-(2-isopropyl-1H-benzo[d]imidazol-1-yl)acetic acid (0.16 mmol, from ChemBridge) and Mukaiyama's reagent (0.38 mmol) in 1.5 ml anhydrous DCM, 4-(4-chloro-2-fluorophenyl)-3-(trifluoromethyl)-1-methyl-1H-pyrazol-5-amine (1d, 0.12 mmol) obtained as described above, triethylamine (0.40 mmol) and 0.5 ml of anhydrous THF were added. The mixture was vortexed and subject to microwave irradiation for 30 min at 75° C. to give a deep green clear solution. Then 80 ml of ethyl acetate was added and washed with 80 ml of saturated NaHCO₃ twice, brine and dried over MgSO₄. After solvent removal and purification on a flash chromatography, slightly brown color solid was obtained. After recrystallization in ethyl acetate/hexane, 45 mg of Compound (1) was given as white powder solid. ¹H NMR (500 MHz, MeOD) δ 7.79 (d, J=7.7 Hz, 1H), 7.62 (dt, J=15.8, 8.2 Hz, 3H), 7.36-7.15 (m, 3H), 5.55 (s, 2H), 3.89 (s, 3H), 3.55-3.44 (m, 1H), 1.47 (d, J=6.9 Hz, 6H); M/Z=494.9 (M+1).

N-(4-(4-chloro-2-fluorophenyl)-1,3-dimethyl-M-pyrazol-5-yl)-2-(2-isopropyl-M-benzo[d]imidazol-1-yl)acetamide (Compound (2))

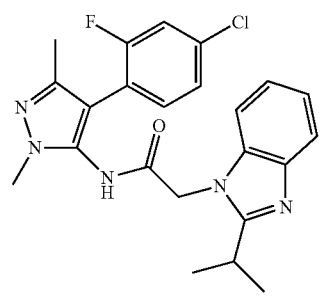

The title compound of the invention was synthesized as described in Scheme 2 below.

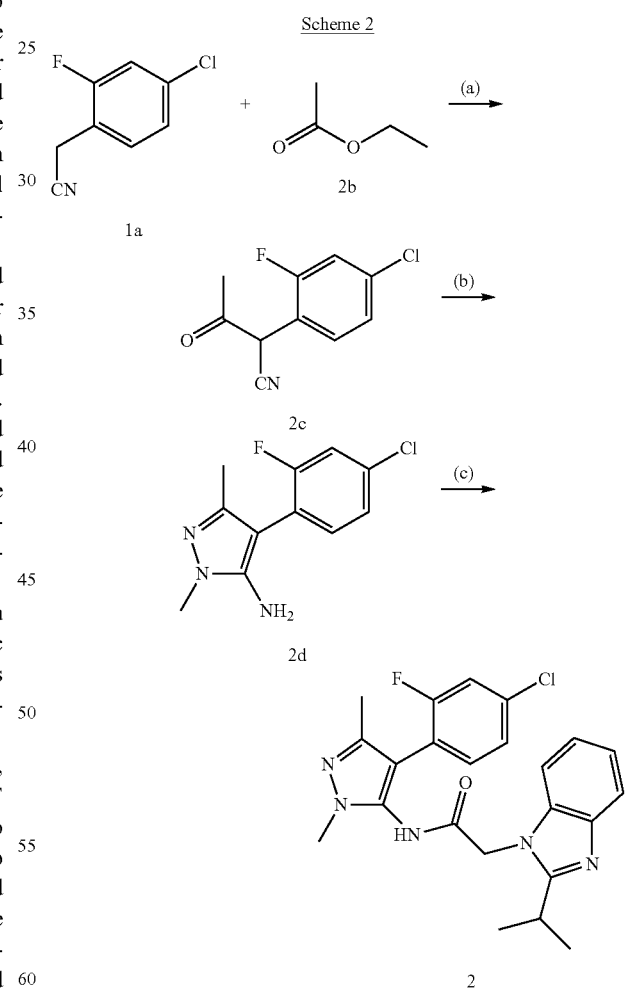

Reagents and conditions: same as in Scheme 1. A mixture of 1.47 ml (15 mmol) of anhydrous ethyl acetate (2b) and 1.2 g (7.1 mmol) of 2-(4-chloro-2-fluorophenyl)acetonitrile (1a) in 10 ml of ethanol was slowly dropped into hot solution of 1.2 g of sodium in 20 ml of ethanol. The mixture was refluxed overnight. The solution turns red. After cooled down, the solution was poured into 250 ml of cold water acidified with 10 ml concentrated HCl. The mixture was extracted with ethyl acetate. The ethyl acetate extraction was washed with water, brine and dried over MgSO₄. Ethyl acetate was removed and the residual reddish oil of 2-(4-chloro-2-fluorophenyl)-3-oxobutanenitrile (2c) was obtained in 1.1 g. The raw material was dissolved in 10 ml of ethanol and used in next step without further purification. A mixture of 2 ml of the above ethanol solution and 125 μl of methylhydrazine with 0.2 ml of concentrated HCl was irradiated in microwave oven at 100° C. for 40 min. The solution was treated with saturated NaHCO₃ and extracted by ethyl acetate. The organic layer was washed with water, brine, dried over MgSO₄ and concentrated. The yellow residue was subjected to flash chromatography purification with MeOH/DCM to give 105 mg of 4-(4-chloro-2-fluorophenyl)-1,3-dimethyl-1H-pyrazol-5-amine (2d) as white solid. 1H NMR (500 MHz, MeOD) δ 7.34-7.16 (m, 3H), 3.58 (s, 3H), 2.03 (s, 3H); M/Z=240.7 (M+1). To a mixture of 2-(2-isopropyl-1H-benzo[d]imidazol-1-yl)acetic acid (0.16 mmol) and Mukaiyama's reagent (0.38 mmol) in 1.5 ml anhydrous DCM, 4-(4-chloro-2-fluorophenyl)-1,3-dimethyl-1H-pyrazol-5-amine obtained as described above (0.12 mmol), triethylamine (0.40 mmol) and 0.5 ml of anhydrous THF were added. The mixture was vortexed and subject to microwave irradiation for 30 min at 75° C. to give a deep green clear solution. Then, 80 ml of ethyl acetate was added and washed with 80 ml of saturated NaHCO₃ twice, brine and dried over MgSO₄. After solvent removal and purification on a flash chromatography, 42 mg of Compound (2) was given as white powder solid. ¹H NMR (500 MHz, MeOD) δ 7.60 (dd, J=6.6 Hz, 1.9 Hz, 1H), 7.35-7.13 (m, 6H), 5.13 (s, 2H), 3.70 (s, 3H), 3.17 (dt, J=13.7 Hz, 6.9 Hz, 1H), 2.14 (s, 3H), 1.36 (d, J=6.8 Hz, 6H); M/Z=440.9 (M+1).

(R)-3-amino-N-(3-(trifluoromethyl)-4-(4-fluorophenyl)-1-methyl-1H-pyrazol-5-yl)-4-(4-fluorophenyl)butanamide (Compound (3))

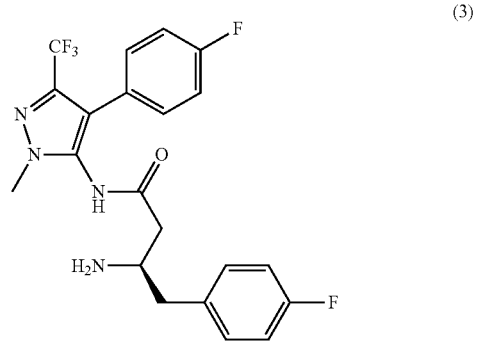 [SMILES: Cn1nc(C(F)(F)F)c(-c2ccc(F)cc2)c1NC(=O)C[C@H](N)Cc1ccc(F)cc1]

(3)

The title compound of the invention was synthesized as described in Scheme 3 below.

Scheme 3

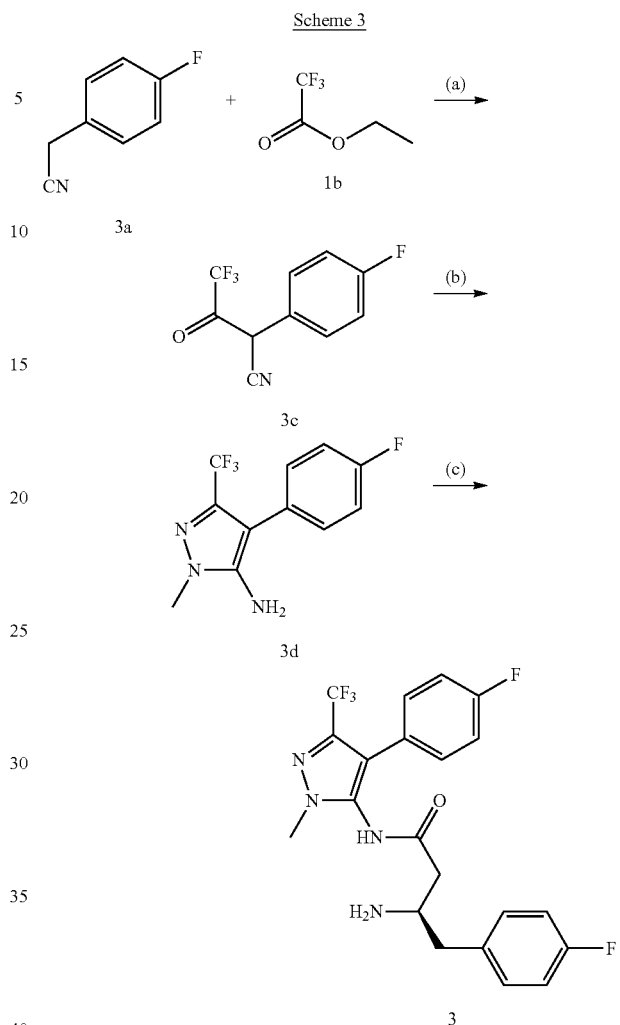

Reagents and conditions: (a) EtONa, EtOH, refluxing; (b) CH₃NHNH₂, HCl, EtOH, MW, 100° C., 40 min; (c) Fmoc-(R)-3-amino-4-(4-fluorophenyl)butanoyl chloride, DCM, then DBU. A mixture of 1.8 ml (15 mmol) of ethyl 2,2,2-trifluoroacetate (1b) and 0.96 g (7.1 mmol) of 2-(4-chloro-2-fluorophenyl)acetonitrile (3a) in 10 ml of ethanol was slowly dropped into hot solution of 1.2 g of sodium in 20 ml of ethanol. The mixture was refluxed overnight. The solution turns red. After cooled down, the solution was poured into 250 ml of cold water acidified with 10 ml concentrated HCl. The mixture was extracted with ethyl acetate. The ethyl acetate extraction was washed with water, brine and dried over MgSO₄. Ethyl acetate was removed and the residual reddish oil of 4,4,4-trifluoro-2-(4-fluorophenyl)-3-oxobutanenitrile (3c) was obtained in 1.3 g. The raw material was dissolved in 10 ml of ethanol and used in next step without further purification. A mixture of 2.8 ml of the above ethanol solution and 125 μl of methylhydrazine with 0.2 ml of concentrated HCl was irradiated in microwave oven at 100° C. for 40 min. The solution was treated with saturated NaHCO₃ and extracted by ethyl acetate. The organic layer was washed with water, brine, dried over MgSO₄ and concentrated. The yellow residue was subjected to flash chromatography purification with MeOH/DCM to give 165 mg of 3-(trifluoromethyl)-4-(4-fluorophenyl)-1-methyl-1H- pyrazol-5-amine (3d) as light yellow solid. $^1$H NMR (500 MHz, CDCl3) δ 7.32 (s, 2H), 7.14 (t, J=8.0 Hz, 2H), 3.76 (d, J=33.5 Hz, 3H), 3.65 (s, 2H). M/Z=260.6 (M+1). To a solution of Fmoc-(R)-3-amino-4-(4-fluorophenyl)butanoyl chloride (43 mg, 0.20 mmol) produced from Fmoc-(R)-3-amino-4-(4-fluorophenyl)butanoic acid (from Chem Impex International) and thionyl chloride in 10 ml of anhydrous DCM were slowly added 3-(trifluoromethyl)-4-(4-fluorophenyl)-1-methyl-1H-pyrazol-5-amine obtained as described above (39 mg, 0.15 mmol) in 5 ml of anhydrous DCM. The reaction mixture was stirred at room temperature overnight. The reaction mixture was quenched with methanol and solvents were removed. The residue was purified via silica gel with MeOH/DCM to obtained Fmoc protected product. Fmoc protected product was dissolved in 10 ml of ethyl acetate and 0.15 mmol of DBU was added. After 20 min, 20 ml of ethyl acetate was added and mixture was washed with 20 ml of water. The organic layer was collected and solvent was removed. The residue was dissolved in MeOH and acidified with 0.2N HCl. The solution was purified via preparatory RP-HPLC, eluting with H$_2$O/CH$_3$CN gradient (+0.05% TFA). Product fractions are collected and concentrated. The residue is dissolved in a small amount of 2M HCl in methanol and, after concentration in vacuo, 50 mg of Compound (3) is obtained as an HCl salt. $^1$H NMR (500 MHz, MeOD) δ 7.40-7.08 (m, 6H), 7.02 (t, J=8.8 Hz, 2H), 3.77 (d, J=15.4 Hz, 3H), 3.37 (dt, J=7.9, 6.6 Hz, 1H), 2.64 (m, 2H), 2.42 (m, 2H). M/Z=439.4 (M+1).

(R)-3-amino-4-(4-fluorophenyl)-N-(4-(4-fluorophenyl)-1,3-dimethyl-1H-pyrazol-5-yl) butanamide (Compound (4))

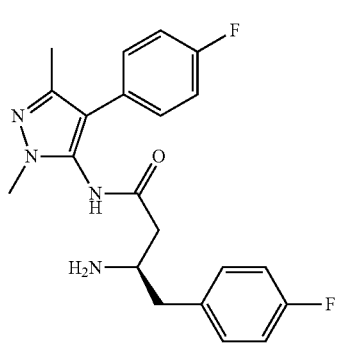

(4)

The title compound of the invention was synthesized as described in Scheme 4 below.

Scheme 4

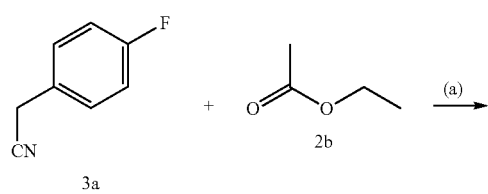

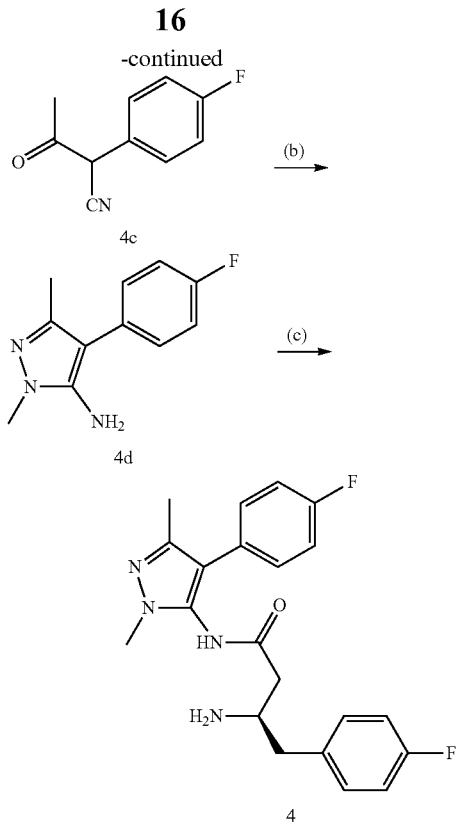

Reagents and conditions: same as in Scheme 3. A mixture of 1.47 ml (15 mmol) of anhydrous ethyl acetate (2b) and 0.96 g (7.1 mmol) of 2-(4-chloro-2-fluorophenyl)acetonitrile (3a) in 10 ml of ethanol was slowly dropped into hot solution of 1.2 g of sodium in 20 ml of ethanol. The mixture was refluxed overnight. The solution turns red. After cooled down, the solution was poured into 250 ml of cold water acidified with 10 ml concentrated HCl. The mixture was extracted with ethyl acetate. The ethyl acetate extraction was washed with water, brine and dried over MgSO$_4$. Ethyl acetate was removed and the residual reddish oil of 2-(4-fluorophenyl)-3-oxobutanenitrile (4c) was obtained in 1.1 g. The raw material was dissolved in 10 ml of ethanol and used in next step without further purification. A mixture of 2.55 ml of the above ethanol solution and 125 μl of methylhydrazine with 0.2 ml of concentrated HCl was irradiated in microwave oven at 100° C. for 40 min. The solution was treated with saturated NaHCO$_3$ and extracted by ethyl acetate. The organic layer was washed with water, brine, dried over MgSO$_4$ and concentrated. The yellow residue was subjected to flash chromatography purification with MeOH/DCM to give 165 mg of 4-(4-fluorophenyl)-1,3-dimethyl-1H-pyrazol-5-amine (4d) as light yellow solid; M/Z=206.3 (M+1). To a solution of Fmoc-(R)-3-amino-4-(4-fluorophenyl)butanoyl chloride (43 mg, 0.20 mmol) produced from Fmoc-(R)-3-amino-4-(4-fluorophenyl)butanoic acid and thionyl chloride in 10 ml of anhydrous DCM were slowly added 4-(4-fluorophenyl)-1,3-dimethyl-1H-pyrazol-5-amine obtained as described above (31 mg, 0.15 mmol) in 5 ml of anhydrous DCM. The reaction mixture was stirred at room temperature overnight. The reaction mixture was quenched with methanol and solvents were removed. The residue was purified via silica gel with MeOH/DCM to obtained Fmoc protected product. Fmoc protected product was dissolved in 10 ml of ethyl acetate and 0.20 mmol of DBU was added.

After 20 min, 20 ml of ethyl acetate was added and mixture was washed with 20 ml of water. The organic layer was collected and solvent was removed. The residue was dissolved in MeOH and acidified with 0.2N HCl. The solution was purified via preparatory RP-HPLC, eluting with $H_2O$/$CH_3CN$ gradient (+0.05% TFA). Product fractions were collected and concentrated. The residue is dissolved in a small amount of 2M HCl in methanol and, after concentration in vacuo, 48 mg of Compound (4) is obtained as an HCl salt.
$^1$H NMR (500 MHz, MeOD) δ 7.35-6.97 (m, 8H), 3.74-3.59 (m, 3H), 3.46-3.35 (m, 1H), 2.77-2.57 (m, 2H), 2.45 (m, 2H), 2.21 (d, J=2.5 Hz, 3H); M/Z=385.5 (M+1).

If the above synthetic methods are not applicable to obtain pyrazole derivatives according to the invention and/or necessary intermediates, suitable methods of preparation known by a person skilled in the art should be used. In general, the synthesis pathways for any individual derivative will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, 2005 and Theodora W. Greene and Peter G. M Wuts in "*Protective Groups in Organic Synthesis*", Wiley Interscience, 4$^{th}$ Edition 2006. Compounds of this invention can be isolated in association with solvent molecules by crystallization from evaporation of an appropriate solvent. The pharmaceutically acceptable acid addition salts of the pyrazole derivatives, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of a pyrazole derivative with a suitable base. Both types of salts may be formed or interconverted using ion-exchange resin techniques.

Example 2

Antimalarial Activities of Compounds of the Invention

The ability of pyrazole derivatives according to the invention to kill *P. falciparum* parasites and/or to inhibit its proliferation is assayed through their ability to inhibit *Plasmodium falciparum* growth determined by 3H-hypoxanthine incorporation. The assay is derived from the method originally described by Desjardin et al., 1979, *Antimicrob. Agents Chemother*, 16: 710-718 which was modified. The method assesses parasite growth as reflected by incorporation of radiolabeled hypoxanthine by parasites. *P. falciparum* in culture are exposed to graded dilutions of test compounds for 48 h and incorporation of 3H-hypoxanthine over the last 24 h into parasite nucleic acids is determined by liquid scintillation spectroscopy. The specific method is described below: The test compounds are diluted by three-fold serial dilutions, in triplicate wells, using low hypoxanthine medium (LHM) RPMI (Roswell Park Memorial Institute medium), 1640, 0.5% Albumax, 0.2% sodium bicarbonate, 0.025M HEPES, 2 mM glutamine, 50 µg/ml Gentamicin, 2.5 µg/ml hypoxanthine, pH 7.35) in sterile flat-bottomed 96 well plates. Final volume in each well is 100 µl. Triplicate control wells contain 100 µl LHM without any inhibitor.

The mixed stage parasitized red blood cells (RBCs), containing greater than 50% ring stage parasites, are diluted to 1% parasitemia using uninfected RBCs, washed two times with LHM, and diluted to 3% hematocrit with LHM. 100 µl of diluted parasites is added to each well. Thus, the final hematocrit is 1.5% with 0.5% parasitemia at the beginning of the assay.

The plates comprising the test wells are placed in a humidified chamber, gassed with 5% $CO_2$, 5% $O_2$, 90% $N_2$, and placed in a 36.5° C. incubator for 24 h. After 24 h incubation, 0.25 µCi of 3H-hypoxanthine in 20 µL LHM is added to each well. Plates are returned to the chamber, gassed, and incubated for an additional 24 h. At the end of the second 24 h incubation, plates are transferred to a −80° C. freezer and stored for a minimum of 2 h. then Plates are thawed and the lysed material is transferred to EasyTabC glass fiber filters (Perkin Elmer; PE) using a Packard Filtermate 196 Cell Harvester. Filters are dried, placed in an Omnifilter Cassette (Perkin Elmer), and 30 µl of Microscint-O-high efficiency liquid scintillation cocktail (PE) is added to each 3 well. The plates are sealed with a Top-Seal for 96 well microplates (Perkin Elmer) and counted using a Packard TopCount-1 microplate liquid scintillation counter. Results are tabulated and graphed using Prism GraphPad software to determine effective $EC_{50}$ values (concentration at which 50% parasite growth inhibition occurs). $EC_{50}$s (nM) for a multidrug-resistant *P. falciparum* line Dd2 are reported in Table 1 below.

TABLE 1

| Compound | $EC_{50}$ (nM) |
|---|---|
| 1 | 0.7 |
| 2 | 5.4 |
| 3 | 0.2 |
| 4 | 8 |
| Reference 1 | 150 |
| Reference 2 | 50 |
| Atovaquone | 1 |
| Artemisinin | 12 |

The antimalarial activities of compounds of the invention have been compared to two other pyrazoles which have been said to show some inhibitory activities against *Plasmodium falciparum* (WO 2009/065096) which have the following structures:

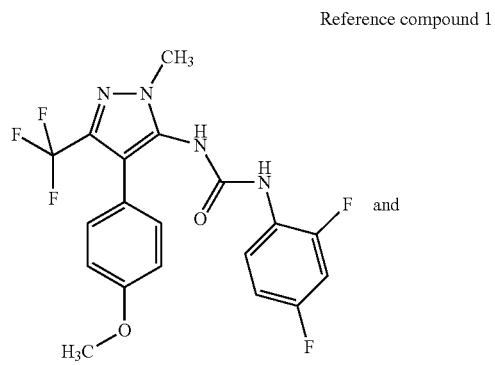

Reference compound 1 and

Reference compound 2

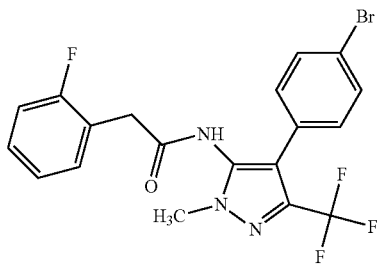

These data show that pyrazole derivatives according to the invention are able to inhibit parasite proliferation in infected human erythrocytes and are more potent than either of the reference compounds.

Compound 2 has also been tested against field isolates of *Plasmodium falciparum* (15 isolates) and *Plasmodium vivax* (15 isolates) using an ex vivo parasite growth inhibition assay as described in Marfurt et al., 2011, *Antimicrob Agents Chemother.*, 55(3): 961. Median $EC_{50}$ values for against these isolates were 15 nM and 10 nM for *P. falciparum* and *P. vivax*, respectively.

Example 3

Anti-Malarial In Vivo Efficacy of Compounds According to the Invention

The ability of pyrazole derivatives according to the invention to show antimalarial efficacy in vivo can be tested by using the protocols described by Jimenez-Diaz et al., 2009, *Antimicrob. Agents Chemother.*, 53:4533-4536. The therapeutic efficacy of compounds of invention against *Plasmodium falciparum* Pf3D70087/N9 growing in peripheral blood of NOD-scidIL2Rγnull mice engrafted with human erythrocytes. Efficacy is assessed by administering varying amounts of single oral doses of compounds per day for four consecutive days (4-day-test) and measuring their effect on blood parasitemia by flow cytometry. This assay provides effective doses of compounds capable of inhibiting 50% ($ED_{50}$) and 90% ($ED_{90}$) levels of parasitemia. Results for the compounds of invention are given in Table 2 below.

TABLE 2

| Compound | $ED_{50}$ (mg/kg per day) | $ED_{90}$ (mg/kg per day) |
|---|---|---|
| 1 | 0.53 | 0.94 |
| 2 | 1.7 | 2.5 |
| 3 | 1.8 | 3.0 |
| 4 | 3.0 | 4.1 |
| Chloroquine | 4.3 | |

The invention claimed is:

1. A pyrazole derivative according to Formula (I),

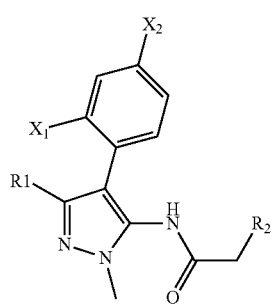

wherein $X_1$ is selected from F and H; $X_2$ is selected from Cl and F; $R^1$ is selected from methyl and trifluoromethyl; $R_2$ is selected from the following groups:

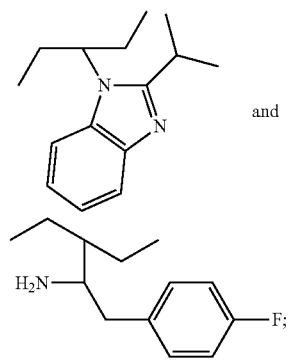

as well as any pharmaceutically acceptable salt, hydrate, solvate, polymorph, tautomers, geometrical isomers, or optically active isomers thereof.

2. The pyrazole derivative according to claim 1 wherein $R_2$ is:

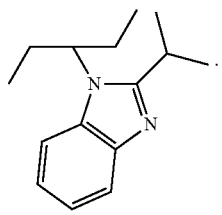 [SMILES: CCC(CC)n1c(C(C)C)nc2ccccc21]

3. The pyrazole derivative according claim 1 wherein $R_2$ is

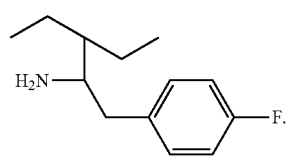

4. The pyrazole derivative according claim 1 selected from the following group:

N-(4-(4-chloro-2-fluorophenyl)-3-(trifluoromethyl)-1-methyl-1H-pyrazol-5-yl)-2-(2-isopropyl-1H-benzo[d]imidazol-1-yl)acetamide;

N-(4-(4-chloro-2-fluorophenyl)-1,3-dimethyl-1H-pyrazol-5-yl)-2-(2-isopropyl-1H-benzo[d]imidazol-1yl)acetamide;

(R)-3-amino-N-(3-(trifluoromethyl)-4-(4-fluorophenyl)-1-methyl-1H-pyrazol-5-yl)-4-(4-fluorophenyl)butanamide; and (R)-3-amino-4-(4-fluorophenyl)-N-(4-(4-fluorophenyl)-1,3-dimethyl-1H-pyrazol-5-yl)butanamide;

as well as any pharmaceutically acceptable salt, hydrate, solvate, polymorph, tautomers, geometrical isomers, or optically active forms thereof.

5. A pharmaceutical composition comprising at least one pyrazole derivative according claim 1 or a pharmaceutically acceptable salt thereof, and a pharmaceutically acceptable carrier, diluent or excipient thereof.

6. The pharmaceutical composition according to claim 5 further comprising an antimalarial co-agent.

7. The pharmaceutical composition according to claim 6 wherein the co-agent is selected from artemisinin or an artemisinin and its derivatives selected from the group consisting of artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl,(1'R,3'S)-(CAS Registry Number: 1193314-23-6), Sulfur, [4-[[2-(1,1-difluoroethyl)-5-methyl[1,2,4] triazolo[1,5-a]pyrimidin-7-yl]amino]phenyl]pentafluoro-(CAS Registry Number: 1282041-94-4), Morpholine, and 4-[2-(4-cis-dispiro[cyclohexane-1,3'-[1,2,4]trioxolane-5',2"-tricyclo [3.3.1.13,7]decan]-4-ylphenoxy)ethyl]-(CAS Registry Number: 1029939-86-3).

8. A method for treating malaria in a patient comprising administering a pyrazole derivative according to claim 1 or a pharmaceutical composition thereof to a patient in need thereof.

9. A method for inactivating parasitic infection in a cell comprising the step of contacting the cell with an effective amount of at least one compound according to claim 1.

10. The method according to claim 9 wherein the pyrazole derivative is to be administered in combination with an antimalarial co-agent.

* * * * *

UNITED STATES PATENT AND TRADEMARK OFFICE
CERTIFICATE OF CORRECTION

PATENT NO. : 9,464,057 B2  
APPLICATION NO. : 14/905369  
DATED : October 11, 2016  
INVENTOR(S) : Burrows et al.

Page 1 of 1

It is certified that error appears in the above-identified patent and that said Letters Patent is hereby corrected as shown below:

In the Specification

Column 12,
Lines 1-3, "N-(4-(4-chloro-2-fluorophenyl)-1,3-dimethyl-M-pyrazol-5-yl)-2-(2-isopropyl-M-benzo[d]imidazol-1-yl)acetamide" should read --N-(4-(4-chloro-2-fluorophenyl)-1,3-dimethyl-1H-pyrazol-5-yl)-2-(2-isopropyl-1H-benzo[d]imidazol-1-yl)acetamide--.

In the Claims

Column 21,
Lines 4-6, Claim 4, "N-(4-(4-chloro-2-fluorophenyl)-1,3-dimethyl-1H-pyrazol-5-yl)-2-(2-isopropyl-1H-benzo[d]imidazol-1yl)acetamide;" should read --N-(4-(4-chloro-2-fluorophenyl)-1,3-dimethyl-1H-pyrazol-5-yl)-2-(2-isopropyl-1H-benzo[d]imidazol-1-yl)acetamide;--.

Signed and Sealed this  
Fourteenth Day of February, 2017

Michelle K. Lee  
*Director of the United States Patent and Trademark Office*